United States Patent [19]

Blom et al.

[11] 4,389,446
[45] Jun. 21, 1983

[54] LIQUID ABSORBING FIBROUS MATERIAL TREATED WITH A WOOD PRESERVATIVE AGENT

[75] Inventors: Cornelis W. Blom, Sassenheim; Jacobus M. van Keulen, Bilthoven, both of Netherlands

[73] Assignee: Woodcap, B.V., Netherlands

[21] Appl. No.: 243,474

[22] Filed: Mar. 13, 1981

Related U.S. Application Data

[62] Division of Ser. No. 889,977, Mar. 24, 1978, Pat. No. 4,265,958.

[30] Foreign Application Priority Data

Mar. 29, 1977 [NL] Netherlands ................. 7703412

[51] Int. Cl.³ ............... A01N 9/02; A01N 17/10; A01N 9/30; B32B 21/04
[52] U.S. Cl. ..................... 428/166; 428/447; 428/452; 428/485; 428/541; 428/907; 428/537; 427/325; 424/288; 424/16; 424/26
[58] Field of Search ........................... 428/537

[56] References Cited

U.S. PATENT DOCUMENTS

| | | |
|---|---|---|
| 1,572,905 | 2/1926 | Stewart ............... 428/541 X |
| 3,318,725 | 9/1967 | Bryan ................. 428/541 X |
| 4,115,130 | 9/1978 | Crump ................ 428/907 X |
| 4,258,090 | 3/1981 | Moraru ............... 428/907 X |
| 4,296,152 | 10/1981 | Kirchner ............. 428/907 X |

FOREIGN PATENT DOCUMENTS

| | | |
|---|---|---|
| 1757476 | 6/1971 | Fed. Rep. of Germany ...... 428/907 |
| 2386991 | 12/1978 | France ..................... 428/907 |

*Primary Examiner*—P. Ives
*Attorney, Agent, or Firm*—Ostrolenk, Faber, Gerb & Soffen

[57] ABSTRACT

A method for the treatment of wood by a wood preserving agent in a liquid or paste-like form, to be positioned (inserted) in a recess in the wood, which recess is subsequently sealed off.

The wood preserving agent contains a water-expelling agent, a water-repellent agent and a biocide.

6 Claims, 3 Drawing Figures

LIQUID ABSORBING FIBROUS MATERIAL TREATED WITH A WOOD PRESERVATIVE AGENT

This is a division of application Ser. No. 889,977, filed Mar. 24, 1978 now U.S. Pat. No. 4,265,958.

BACKGROUND OF THE INVENTION

The invention relates to a method for the treatment of wood using a wood preservative in liquid or paste-like form. Such a method for the treatment of wood using a biocide in a liquid medium is already known. One difficulty of this known method is that the penetrating capacity of the composition containing the biocide into the wood is extremely low. Attempts had been made to improve this by executing treatment under pressure, and some small improvements has been achieved, but even so this is inadequate to provide a treated wood which, when exposed to weather conditions, will remain unattacked by fungi and other micro-organisms.

One further difficulty of the known methods is that the personnel who have to carry out the treatment are directly exposed to the effects of the composition, so that if this contains toxic fungicidal substances, special precautions have to be taken.

One further difficulty of the known methods is that under the influence of weathering, the fungicidal substances can be leached out of the wood very quickly, so that the wood is again exposed to the unimpeded action of fungi, with all the associated disadvantages. The treated wood can be sealed off by a covering layer, but particularly at the angle joints of window frames, where two frame sections are connected with each other, even a short period after application of the paint layer a seam forms as a result of expansion and contraction due to high or low external temperatures.

As a result of the latter-mentioned phenomenon, in spite of good maintenance of many buildings, wood rot is observed in window frames and door frames at the angle points on these frames. Repairs to these attacked locations incur high costs and cannot be undertaken immediately.

The present invention relates to a method for the treatment of wood using a liquid wood preservative whereby all the abovementioned difficulties are avoided.

SUMMARY OF THE INVENTION

The aim of the present invention is achieved in that a wood preservative is incorporated in a recess made in the wood and subsequently the recess is sealed.

By initially providing a recess in the wood, for example by drilling, and subsequently inserting a wood preservative in this recess, followed by the sealing of this recess, a reservoir is provided for a wood preservative in the wood which can subsequently continually supply the said preserving agent. The wood preservative penetrates extremely gradually into the wood located adjacent to the recess. In this way, considerable savings are obtained as compared with the known methods. For example, large quantities of solvent which are used with the known methods and which are lost, can be saved, while furthermore after this treatment the wood material can be painted directly.

After the known method of impregnation of wood using salts it is necessary to wait 6 to 10 weeks before a paint coating can be applied. When using organic solvents, the waiting time is 1 to 3 days. Furthermore, using the method in accordance with the present invention, it is also possible to treat types of wood (such as meranti) into which, normally, wood preservatives cannot penetrate from outside.

Finally the fire resistance of the wood is increased because, as compared with known methods, much less solvent is present in the wood than is the case with vacuum-pressure impregnation methods.

Furthermore, the method in accordance with the invention offers the advantage that the treatment can be restricted to the portions of the wood prone to attack, such as those adjacent to the angle connections of frames. Finally the method is not affected by the season of the year.

Preferably the agent containing the wood preservative consists of a water-expelling liquid medium, especially an organic solvent together with an organosilicon compound or a solid paraffin as water repellent agents.

In this way the water present in the wood is displaced by the water-expelling medium, so that the moisture content of the wood drops below 21%, a value at which no fungal growth can occur. Furthermore, this prevents corrosion of corrodible metals such as nails in the wood.

When using an organo-silicon compound which on curing transforms into a non-adhesive hard polysiloxane, we furthermore obtain an action which tends to reinforce the wood skeleton, so that wood which has been already attacked can be preserved once more without it being replaced by new wood material.

It is especially advantagous to insert a biocide into the recess, particularly a fungicidal agent. We then obtain wood having a biocide impregnant which penetrates slowly into the wood and which can never be completely leached out under the effect of weathering. In those cases where same leaching occurs, this is made up directly by new biocide from the recess.

In this way, it is possible to prevent the growth in wet wood of wood-attacking fungi (Basidiomycetes) and fungi which discolor wood (Ascomycetes) when using fungicidal biocides, also of algae (Pleurococcus) possibly using appropriate agents.

On the other hand, it is possible in this way to counteract attack on wood having low moisture content by insects such as the house beetle (*Hylotrupus bajulus*) and woodworm (*Anobium punctatum* or *Luctunus brunius*), or by bacteria which attack wood.

It is particularly suitable to insert into the recess a composition consisting of a biocide with an evaporative water-expellent solvent. This evaporative solvent is preferably used in an amount of at least 5% and consists of e.g. tetralin, aliphatic or aromatic hydrocarbons whether or not substituted and/or halogenated, ketones, esters, alcohols and ethers. As a result of evaporation of the solvent, the biocide is entrained into the wood and consequently the biocide penetrates very deeply into the wood.

It is extremely suitable to employ a solvent which evaporates slowly, so that very gradual impregnation of the wood around the recess is obtained, thus giving extremely good penetration of the biocide into the wood.

Concerning fungicides, it is recommended that a fungicide be employed with low volatility, combined with a fungicide of high volatility, thus giving an optimum action on the part of the fungicide after a very short period. The most volatile fungicide will penetrate extremely rapidly into the wood, but can admittedly easily evaporate from this, after which the less volatile fungicide will replace any quantity of the more volatile fungicide which has disappeared.

The method in accordance with the invention is particularly suitable for treatment of timber in existing structures, such as door and window frames, which under the effect of weathering are extremely prone to attack by fungi.

In such a case, a considerable amount of moisture is present in the wood, more than 21% wood moisture content, whereby difficulties can be encountered in connection with the penetration of the fungicide in and around the attacked locations in the wood, particularly the angle points of frames.

With particular advantage, one can then use a composition consisting of a biocide such as tributyl tin oxide or a chlorinated hydrocarbon as a water-expelling solvent. This water-expelling solvent can comprise the said organo-silicon compound as water repelling agent, especially a siloxane compound which transforms into a non-adhesive polysiloxane. In such a case, the water-expelling solvent together with the organosilicon compound while penetrating into the wood displaces the moisture present there and at the same time entrains the biocide present in the composition. After a fairly short period, the moisture at the attacked locations will have been expelled and the residual wooden skeleton will have been intimately impregnated by a biocidal agent, originating from the composition, while on curing, the water-repelling organo silicon compound contributes toward increasing the rigidity of the structure. The presence of a topping-up reservoir of water-expelling and/or biocidal agent accomodated in a recess in the wood furthermore offers the major advantage that even in the event of leaching from the surface of the wood, new supplies of preservative can be made available immediately, so that there is practically no possibility of attack by wood fungi in the event of damage to a paint coating on the wood.

On the other hand, by inserting a suitable biocide, it is possible to counteract attack on dry wood by woodworm in buildings, whereby in comparison with known methods of preservation, species such as pigeons suffer no disadvantage from this. With these known methods an agent which attacks woodworm is injected by needle under pressure into a joist, whereby the toxic agent can easily emerge from the wood with serious consequences for pigeons and the like; frequently these animals die as a result of poisoning by such agents.

To facilitate the insertion of the agent containing the wood preserving substance into the recess, it is recomended that the composition be incorporated in absorbent material.

It is very appropriate if the composition is incorporated in a capsule having an aperture, which can be opened when the seal is placed on the recess. This embodiment is particularly advantageous because in such a case, the persons who undertake the treatment are working with a composition to which they are not exposed because the toxic substances possibly present in the composition are only released at the moment when the recess in the wood is sealed off from the outside, such as by a plastic cover. This cover material can be subsequently painted over in the normal manner, so that, for example in the case of a frame, it is not possible even from the outside to perceive that the relevant treatment has been carried out.

When using a capsule, it is most appropriate if this is surrounded by a layer of absorbent material, so that extremely gradual release of the composition to the wood from the absorbent material is possible.

By including a stiffening substance in the absorbent material, whose action is obtained mainly after evaporation of the solvent and disappearance of the fungicidal products, we achieve extremely good sealing and filling out of the recess. Furthermore, it is easy to later insert a new quantity of wood preservative agent into the recess, after removal of the plug or capsule inserted previously.

The invention similarly relates to wood impregnated by a wood preservative agent, wherein the wood possesses a recess in which a wood preservative agent is incorporated, the said recess being terminated by a covering material, and where preferably a biocide is present together with a solvent, particularly a water-expelling solvent, in the recess. More than 5% of a water-expelling solvent such as tetralin, aliphatic hydrocarbons and aromatic hydrocarbons whether or not substituted and/or halogenated ketones, esters, alcohols, glycols, ethers is used.

It is advisable that the biocide in the recess should be a biocide of low volatility or a biocide of high volatility, preferably a mixture of both. The biocide should advisably be a fungicide.

The wood should preferably be impregnated with a biocide, advisably a fungicidal substance, in the vicinity of the recess.

In the recess, the wood preservative agent is advisably in the form of an opened capsule, advisably surrounded by an absorbent material.

The invention similarly relates to a cartridge with absorbent material, with water-expelling agent or wood preservative biocide perhaps incorporated in a separate holder.

SHORT SURVEY OF THE DRAWINGS

FIG. 1 denotes a section through a wooden object provided with a drilled recess in which there is an absorbent material with a fungicidal or water-expelling agent;

FIG. 2 shows the same recess in which there is a capsule surrounded by absorbent material, and FIG. 3 shows a capsule in which the water-expelling or biocidal agent is under pressure in the capsule.

DESCRIPTION OF PREFERRED EMBODIMENTS

Example I

Figure 1:
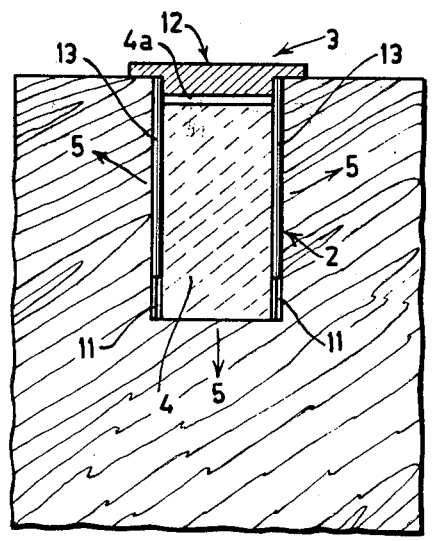
Figure 3:
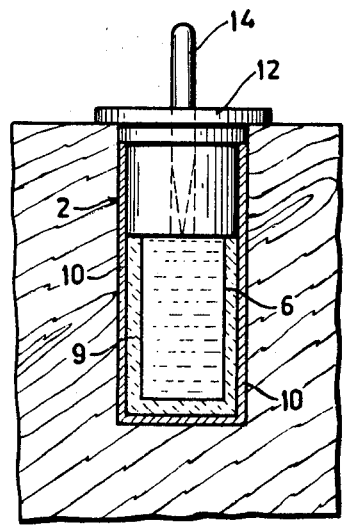

In a wet timber joist having a thickness of 5 cm, a recess 2 is drilled which is capable of being sealed at the top 3. The recess 2 does not need to be cylindrical but can also be tapered in shape. An absorbent plug 4 (see FIG. 1) consisting for example of cotton, wool or fiber material in which a liquid composition is absorbed consisting of a polysiloxane compound which can form a non-adhesive polysiloxane in the dry state is inserted in the recess 3. The composition contains 2% of polysiloxane, 5% of tributyltin and for the remaining part, tetralin.

After insertion of the plug 4, the top side 3 of the recess 2 is sealed off by means of a plastic cover, e.g. a polythene cap 4a.

After roughly 14 days, significant penetration of the water-repellent silicon compound into the timber is observable, in the direction toward the arrows 5.

It will be obvious that particularly when locating such a recess in the vicinity of the transition between two portions of wood in a frame, the water-repellent silicon compound can move easily toward the top surface of the associated timber portions.

As a result of expulsion of the water, the moisture content of the wood will drop below 21%, thus precluding fungal growth. The curing of the silicon compound occurring during this period will furthermore considerably stiffen the structure of the wood.

The plug 4 should preferably be incorporated in a sealing covering 11 made of aluminum foil, which covering 11 is stripped off from the plug during the application of the cover 12, which is provided with pins 13 which strip off the covering.

Example II

Insert a plug 4 (FIG. 1) containing a 2% siloxane compound and 10% tributyl tin oxide together with 88% tetralin as fungicide. The siloxane compound together with tetraline expels the water while entraining the fungicide and penetrates up to the top surface of the wood.

In the event of leaching out as a result of penetrating rain, new supplies of fungicide will be provided immediately from the fungicide reservoir in the form of the plug 4 which is located in the recess 2.

After application of the polythene covering cap 12, the entire wooden surface can normally be covered by a coloured paint coating.

Example III

Figure 2:
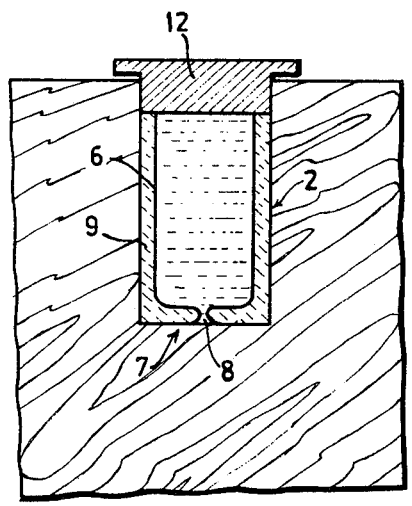

In the recess 2 (see FIG. 2) insert a polythene capsule 6 which is filled with the composition of a polysiloxane compound (2%) and 10% tributyl tin oxide as well as tetralin. At its end 7, this capsule is provided with a hole 8 which opens up to a certain extent when pressure is exerted on the polythene capsule 6. A layer of cellulose wadding 9 is placed around the polythene capsule.

After inserting the capsule 6 in the recess 2, install a cover 12 which penetrates into the recess 2 to such an extent that pressure is exerted on the polythene capsule 6, and consequently the aperture 8 at the end of the capsule opens. By this means the liquid composition consisting of 2% polysiloxane together with 5% tributyl tin oxide and 93% tetralin in the absorbent layer 9 (e.g. cotton wool) can pass through and from this point penetrate into the wood material located around the recess 2.

In the liquid composition which is located in the capsule 6, there is a tributyl tin oxide of high volatility and a tributyl tin oxide of low volatility so as to insure optimum action on the part of the fungicide.

Above we have always mentioned a polysiloxane compound together with an organic solvent as the water-expelling solvent, but it should be made clear that other water-expelling products together with organic solvents can also be employed; preferably organic solvents which exhibit low volatility and thus ensure optimum penetration of solvent with fungicide into the wood around the recess should be used. One major advantage in this respect is that the persons who are treating the wood in accordance with the method in this invention do not come into contact with toxic substances such a tributyl tin chloride.

Example IV

In a recess 2, insert a capsule 6 surrounded by an absorbent layer 9, this layer 9 again being surrounded by a perforated plastic cylinder 10. The capsule 6 is provided with an impact pin 14 which can be pressed through the capsule so that the contents of the capsule, solid paraffin m.p. 40° C. (2%) with 10% tributyl tin oxide and tetralin 88% can penetrate into the porous layer. The contents of the capsule 6 are under pressure, but this is not essential. For checking purposes, tracers can be included in the composition so as to monitor penetration.

Example V

A porous material impregnated with silane compound and tributyl tin oxide is placed between a tongued and grooved joint. The effective compounds penetrate into the wood.

What is claimed is:

1. A liquid absorbing fibrous material provided with a sealed covering and having absorbed a composition for treating wood with a wood preservative agent in liquid or paste-like form comprising a liquid water expelling agent in an amount of at least 5%, biocide and water expelling agent.

2. The material of claim 1, wherein said composition comprises polysiloxane, tributyl tin oxide and tetralin.

3. The material of claim 1 in the form of a sealed capsule.

4. The material of claim 1 surrounded by a layer of porous material.

5. The material of claim 1 wherein said water repelling agent is a polysiloxane or paraffin.

6. The material of claim 5 wherein said biocide is tributyl tin oxide or pentachlorophenol.

* * * * *